United States Patent
Ogasawara

(10) Patent No.: US 9,839,412 B2
(45) Date of Patent: Dec. 12, 2017

(54) ULTRASONIC IMAGE DISPLAY APPARATUS AND CONTROL PROGRAM FOR CONTROLLING THE SAME

(71) Applicant: GE MEDICAL SYSTEMS GLOBAL TECHNOLOGY COMPANY, LLC, Waukesha, WI (US)

(72) Inventor: Masafumi Ogasawara, Tokyo (JP)

(73) Assignee: GE MEDICAL SYSTEMS GLOBAL TECHNOLOGY CO. LLC, Waukesha, WI (US)

( * ) Notice: Subject to any disclaimer, the term of this patent is extended or adjusted under 35 U.S.C. 154(b) by 985 days.

(21) Appl. No.: 14/095,316

(22) Filed: Dec. 3, 2013

(65) Prior Publication Data
US 2014/0155749 A1    Jun. 5, 2014

(30) Foreign Application Priority Data

Dec. 4, 2012 (JP) .................................. 2012-265211

(51) Int. Cl.
*A61B 8/08* (2006.01)
*A61B 8/00* (2006.01)

(52) U.S. Cl.
CPC .......... *A61B 8/5292* (2013.01); *A61B 8/0891* (2013.01); *A61B 8/4254* (2013.01); *A61B 8/5253* (2013.01)

(58) Field of Classification Search
CPC ... A61B 8/5292; A61B 8/5253; A61B 8/0891; A61B 8/4254
See application file for complete search history.

(56) References Cited

U.S. PATENT DOCUMENTS

| 5,485,845 | A | * | 1/1996 | Verdonk | ................. | A61B 8/12 600/463 |
| 6,258,031 | B1 | | 7/2001 | Sunagawa et al. | | |
| 7,044,913 | B2 | | 5/2006 | Shiki | | |

(Continued)

FOREIGN PATENT DOCUMENTS

| JP | 09-201358 | 8/1997 |
| JP | 10-295691 | 11/1998 |

(Continued)

OTHER PUBLICATIONS

Office Action issued in connection with corresponding KR Application No. 10-2013-0149267 dated Mar. 22, 2016.

*Primary Examiner* — Long V Le
*Assistant Examiner* — Colin T Sakamoto

(57) ABSTRACT

An ultrasonic image display apparatus is provided. The ultrasonic image display apparatus includes an ultrasonic probe configured to move while in contact with a test object and configured to transmit and receive ultrasonic waves to and from the test object to obtain echo signals from a three-dimensional region of the test object, a parameter calculation section configured to calculate a parameter related to a moving velocity of the ultrasonic probe, a data generation section configured to generate data based on the echo signals of a plurality of frames, by selecting the frames in accordance with the parameter calculated by the parameter calculation section so that the echo signals of the frames used for generating the data are acquired within a required range, and a display section configured to display an ultrasonic image generated based on the data.

12 Claims, 13 Drawing Sheets

(56) References Cited

U.S. PATENT DOCUMENTS

| | | |
|---|---|---|
| 8,394,024 B2 | 3/2013 | Miyama et al. |
| 8,475,382 B2 | 7/2013 | Miyama et al. |
| 8,577,105 B2 | 11/2013 | Abe et al. |
| 2003/0120171 A1* | 6/2003 | Diamantopoulos .... A61B 5/015 600/549 |
| 2009/0318809 A1 | 12/2009 | Okamura et al. |

FOREIGN PATENT DOCUMENTS

| | | |
|---|---|---|
| JP | 2000-000238 | 1/2000 |
| JP | 3365929 B2 | 1/2003 |
| JP | 2003-325519 | 11/2003 |
| JP | 2009-060943 | 3/2009 |
| JP | 2010000143 A | 1/2010 |

* cited by examiner

MOVING DIRECTION OF ULTRASONIC PROBE

ULTRASONIC IMAGE DISPLAY APPARATUS AND CONTROL PROGRAM FOR CONTROLLING THE SAME

CROSS REFERENCE TO RELATED APPLICATIONS

This application claims the benefit of Japanese Patent Application No. 2012-265211 filed Dec. 4, 2012, which is hereby incorporated by reference in its entirety.

BACKGROUND OF THE INVENTION

The present invention relates to an ultrasonic image display apparatus for displaying ultrasonic images based on echo signals from the three-dimensional region of a test object, and a control program for controlling the ultrasonic image display apparatus.

For example, blood vessels of the test object may be observed by ultrasonic diagnostic equipment using contrast images. It is useful to get an overall picture of the blood vessels running through, say, a tumor and its surroundings by means of blood vessel contrast image. However, since two-dimensional contrast image depicts only those blood vessels that are present on a specific cross section, it is difficult to obtain a three-dimensional overall picture of the blood vessels.

Given that difficulty, there exists ultrasonic diagnostic equipment that displays two-dimensional projection images based on projection data generated from echo signals of a plurality of frames, i.e., generated either from the data obtained by integrally adding up the echo signals of the plurality of frames acquired from the three-dimensional region of the test object, or from the data using maximum signal values of the echo signals of the plurality of frames (e.g., see Japanese Patent Publication No. 3365929).

The above-mentioned ultrasonic diagnostic equipment acquires the echo signals from the three-dimensional region of the test object by having an ultrasonic probe moved over the test object to transmit and receive ultrasonic waves thereto and therefrom. Since it is difficult to keep identical the velocity at which the operator moves the ultrasonic probe in different tests, the time required for the probe to move the same distance may differ from test to test.

Ordinarily, however, the range in which to obtain echo signals used for generating the above-mentioned projection data is set in accordance with the number of frames and the time involved. The frame count and the time are input by the operator and remain constant regardless of the moving velocity of the ultrasonic probe. This means that the range in which to obtain the echo signals used for generating the projection data (i.e., range of the ultrasonic probe in the direction of its movement) varies depending on the moving velocity of the ultrasonic probe. Thus if the moving velocity of the ultrasonic probe is low, it is impossible to acquire the projection data using the echo signals over a sufficient range, which may result in the display of a projection image showing the target blood vessels being truncated halfway.

In view of the problem above, there is a need for keeping constant the range in which to obtain the echo signals used for generating the projection data regardless of the variable moving velocity of the ultrasonic probe.

BRIEF DESCRIPTION OF THE INVENTION

In one aspect, and ultrasonic image display apparatus is provided. The ultrasonic image display apparatus includes an ultrasonic probe which is moved while in contact with a test object and which transmits and receives ultrasonic waves thereto and therefrom so as to obtain echo signals from a three-dimensional region of the test object, a parameter calculation section which calculates a parameter related to a moving velocity of the ultrasonic probe, a data generation section which generates data based on the echo signals of a plurality of frames, by selecting the frames in accordance with the parameter calculated by the parameter calculation section so that the echo signals of the frames used for generating the data are acquired within a required range, and a display section which displays an ultrasonic image generated based on the data.

According to the above aspect, the data is generated by selecting the frames in accordance with the moving velocity detected by the velocity detection section, so that the echo signals of the frames used for generating the data are obtained within a required range. Thus even when the moving velocity of the ultrasonic probe varies, the range in which to obtain the echo signals for generating the data can be kept constant.

DETAILED DESCRIPTION OF THE INVENTION

Figure 1:
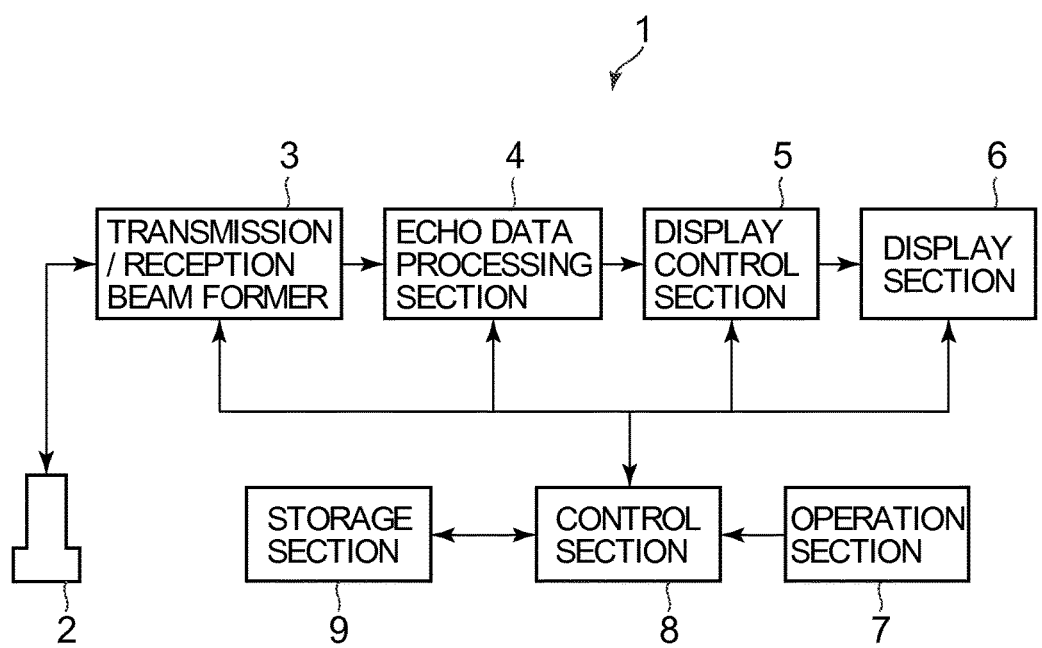
FIG. 1 is a block diagram showing a typical overall structure of ultrasonic diagnostic equipment as an exemplary embodiment.

An exemplary embodiment will be explained below in detail with reference to FIGS. 1 through 10. Ultrasonic diagnostic equipment 1 shown in FIG. 1 includes an ultrasonic probe 2, a transmission/reception beam former 3, an echo data processing section 4, a display control section 5, a display section 6, an operation section 7, a control section 8, and a storage section 9. The ultrasonic diagnostic equipment 1 is an example of the ultrasonic image display apparatus.

The ultrasonic probe 2 is structured to have a plurality of ultrasonic transducers (not shown) arranged in an array. The ultrasonic transducers transmit ultrasonic waves to a test object and receive echo signals therefrom.

The transmission/reception beam former 3 supplies the ultrasonic probe 2 with an electric signal based on control signals from the control section 8, the electric signal causing the ultrasonic probe 2 to transmit ultrasonic weaves under predetermined scanning conditions. Also, the transmission/reception beam former 3 performs signal processing such as A/D conversion and a phasing process on the echo signals received through the ultrasonic probe 2, and outputs the processed echo data to the echo data processing section 4.

Figure 2:
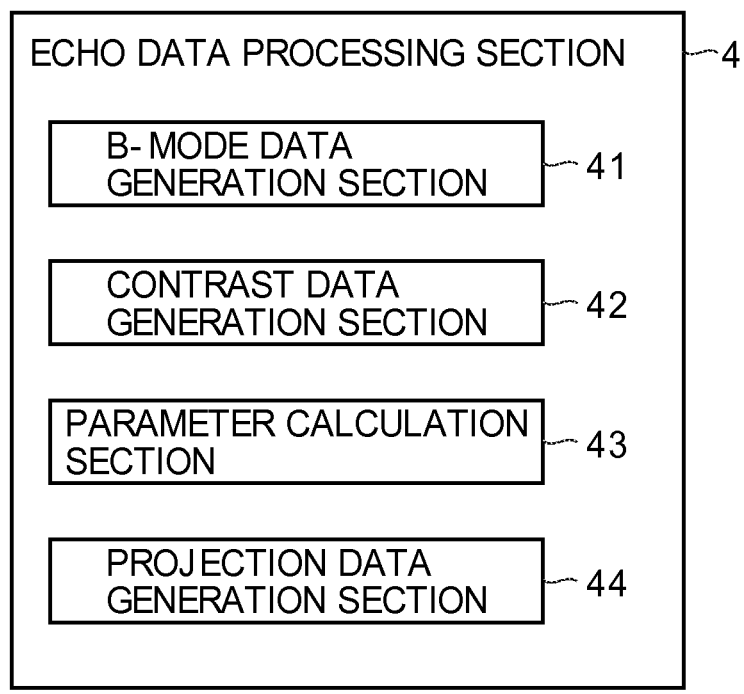
FIG. 2 is a block diagram showing a structure of an echo data processing section of the ultrasonic diagnostic equipment indicated in FIG. 1.

The echo data processing section 4 performs signal processing for ultrasonic image generation on the echo data output from the transmission/reception beam former 3. For example, as shown in FIG. 2, the echo data processing section 4 includes a B-mode data generation section 41, a contrast data generation section 42, a parameter calculation section 43, and a projection data generation section 44.

The B-mode data generation section 41 generates B-mode data by carrying out B-mode processing including a logarithmic compression process and an envelope demodulation process.

The contrast data generation section 42 generates contrast data by performing a process for generating contrast-enhanced images obtained with a contrast medium administered to the test object, the process being carried out on the echo data output from the transmission/reception beam former 3. For example, the contrast data generation section 42 performs a filtering process for extracting the harmonic content from the echo signals. Also, the contrast data generation section 42 may extract the echo signals from the contrast medium using the technique of pulse inversion. Alternatively, the contrast data generation section 42 may extract the echo signals from the contrast medium by subtracting the echo data based on the echo signals obtained from the transmission of ultrasonic waves of different amplitudes (the process is called amplitude modulation).

The parameter calculation section 43 calculates a parameter related to the moving velocity of the ultrasonic probe 2 (parameter calculation function). The section will be discussed later in more detail. The parameter calculation section 43 is an example of the parameter calculation section. The parameter calculation function is an example of the parameter calculation function.

The projection data generation section 44 generates projection data reflecting the above-mentioned contrast data of a plurality of frames (projection data generation function). The section will be discussed later in more detail. The projection data generation section 44 is an example of the data generation section. The projection data generation function is an example of the data generation function.

The display control section 5 generates ultrasonic image data using a scan converter to perform scan conversion on the data input from the echo data processing section 4, and causes the display section 6 to display an ultrasonic image based on the ultrasonic image data. For example, the display control section 5 scan-converts the B-mode data to generate B-mode image data and causes the display section 6 to display a B-mode image based on the B-mode image data. Also, the display control section 5 scan-converts the projection data to generate projection image data and causes the display section 6 to display a projection image based on the projection image data. The projection image will be discussed later.

The display section 6 is composed of an LCD (liquid crystal display), a CRT (cathode ray tube) or the like. The operation section 7 is structured to include a keyboard and a pointing device (not shown) for the operator to input instructions and information.

The control unit 8 is a CPU (central processing unit) that reads control programs from the storage section 9 and causes the components of the ultrasonic diagnostic equipment 1 to perform their functions with the programs. For example, the functions of the transmission/reception beam former 3, echo data processing section 4, and display control section 5 may be implemented by the control programs. The functionality of the echo data processing section 4 includes such functions as the parameter calculation function and projection data generation function, to be discussed later.

The storage section 9 is an HDD (hard disk drive) or a semiconductor memory, for example.

Figure 3:
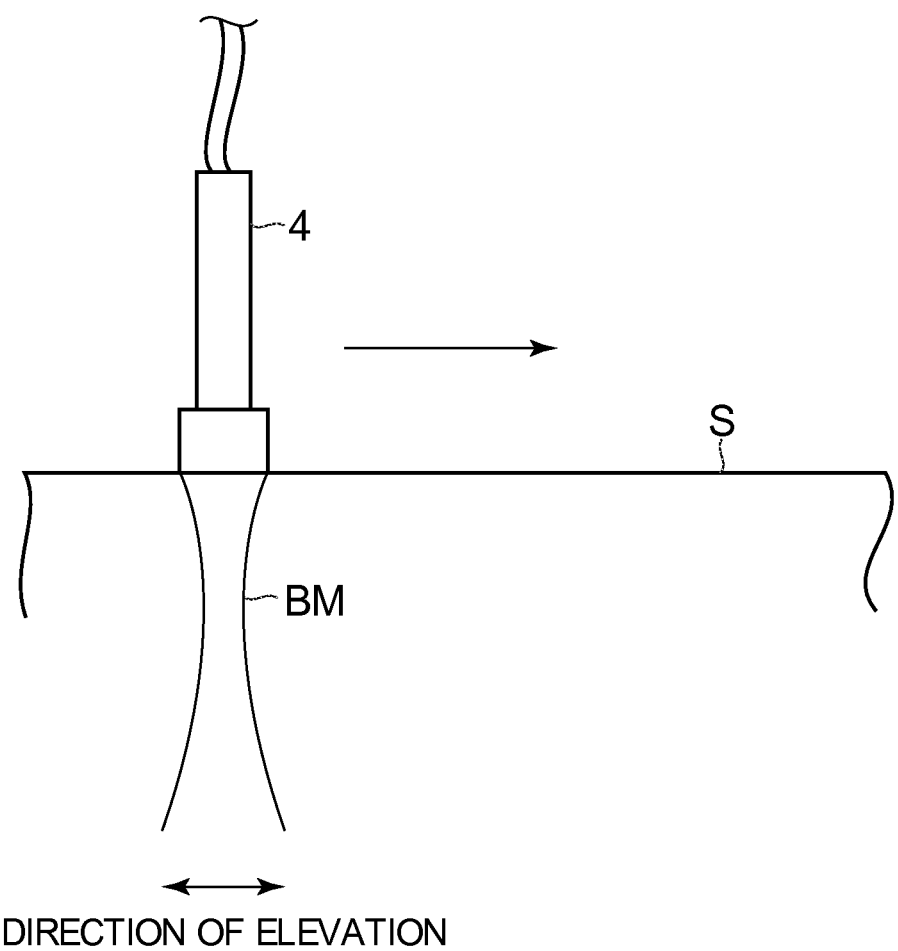
FIG. 3 is a view for explaining a parallel displacement of an ultrasonic probe transmitting and receiving ultrasonic waves.
Figure 4:
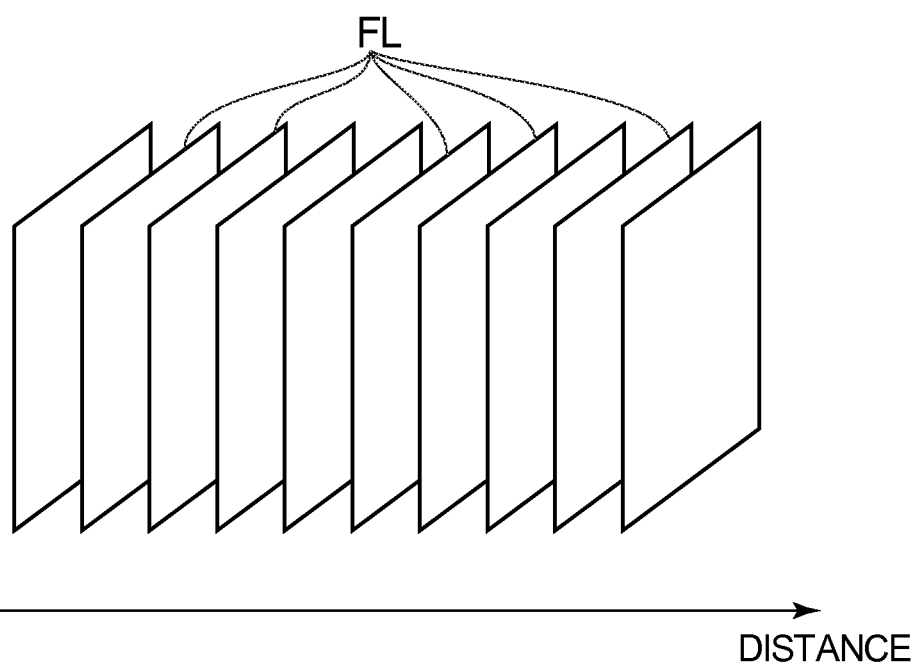
FIG. 4 is a view for explaining how echo signals of a plurality of frames are acquired through parallel displacement of the ultrasonic probe.

What follows is an explanation of how the ultrasonic diagnostic equipment of this example works. First, the operator brings the ultrasonic probe 2 into contact with a body surface S of the test object and gets the probe 2 to transmit and receive ultrasonic waves. In FIG. 3, reference character BM denotes an ultrasonic beam. The operator then causes the ultrasonic probe 2 transmitting and receiving ultrasonic waves to make a parallel displacement over the body surface S. This allows echo signals of a plurality of frames to be acquired from a three-dimensional region of the test object, as shown in FIG. 4. Reference character FL stands for a frame. FIG. 4 illustrates only the concept of frames and does not show echo signals.

The ultrasonic waves are transmitted and received to and from the test object to which the contrast medium has been administered.

When the echo signals are obtained, the B-mode data generation section 41 generates B-mode data about each frame based on the echo signals. Also, the contrast data generation section 42 generates the contrast data based on the echo signals. Next, the projection data generation section 44 generates projection data based on the contrast data of a plurality of frames. The display control section 5 may generate B-mode image data based on the B-mode data and cause the display section 6 to display a B-mode image. Also, the display control section 5 may generate projection image data based on the projection data and cause the display section 6 to display a projection image. The projection image is an image obtained when a three-dimensional region including the projection data of a plurality of frames is projected onto a two-dimensional plane.

Figure 5:
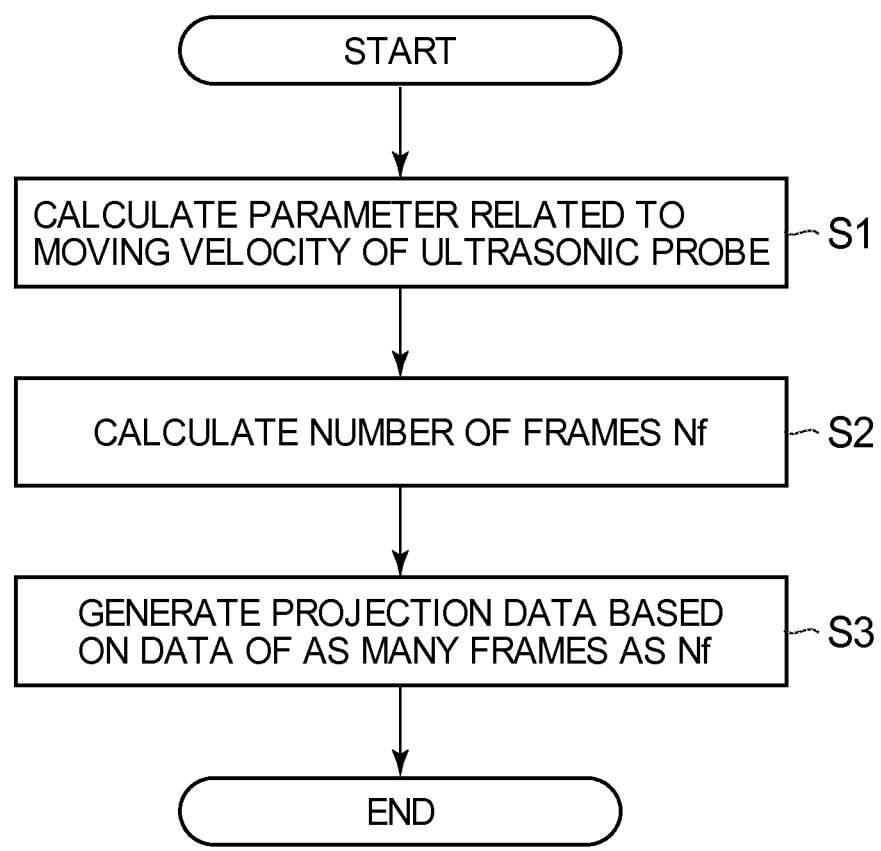
FIG. 5 is a flowchart showing a process for generating projection data.

Generation of the projection data is explained below with reference to the flowchart of FIG. 5. First in step S1, the parameter calculation section 43 calculates a parameter related to the moving velocity of the ultrasonic probe 2. The parameter calculation section 43 calculates the parameter related to the moving velocity of the ultrasonic probe 2 from the B-mode image data generated by the display control section 5. Specifically, the parameter calculation section 43 performs a correlation calculation on the B-mode image data of one frame and on the B-mode image data of another frame. The correlation calculation is not limited to the data between two frames; it may be carried out on the B-mode image data of one frame and on the B-mode image data of a plurality of other frames.

For example, the correlation calculation may also be performed on a region of interest set in a B-mode image. The operator may set the region of interest in the B-mode image displayed on the display section 6 before moving the ultrasonic probe 2.

A correlation coefficient C obtained through the correlation calculation by the parameter calculation section 43 is the parameter related to the moving velocity. What follows is a more specific explanation. The higher the moving velocity of the ultrasonic probe 2 is, the longer the distance between two adjacent frames becomes. In that case, the correlation between the B-mode images of the frames is smaller and so is the correlation coefficient C. Conversely, the lower the moving velocity of the ultrasonic probe 2 is, the shorter the distance between two adjacent frames becomes. In this case, the correlation between the B-mode images of the frame is larger and so is the correlation coefficient C.

Next in step S2, the projection data generation section 44 calculates the number of frames used for generating projection data. Based on the correlation coefficient C calculated in step S1, the projection data generation section 44 calculates the number of frames Nf for projection data generation so that the range in which to acquire the echo signals of the frames for projection data generation becomes a required range.

Figure 6:
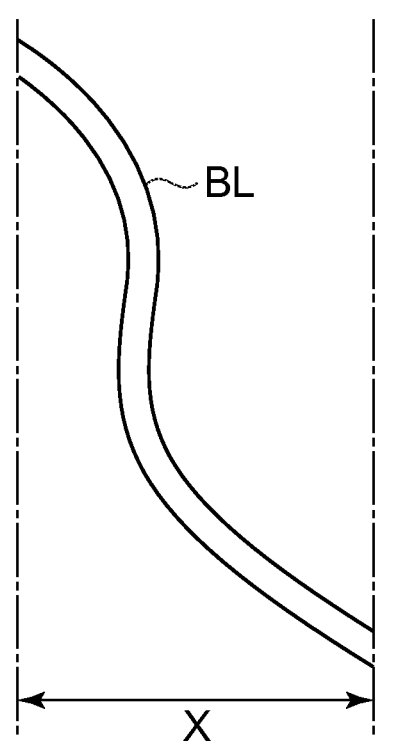
FIG. 6 is a view for explaining a required range.

The range in which to acquire the echo signals signifies a range in the moving direction of the ultrasonic probe 2. The required range may be set by the operator using the operation section 7. For example, as shown in FIG. 6, the required range may be set to a range X that covers the entire blood vessel BL that the operator wants to observe. Alternatively, the required range may be set by the operation section 7 using values representative of distances, for example.

Figure 7:
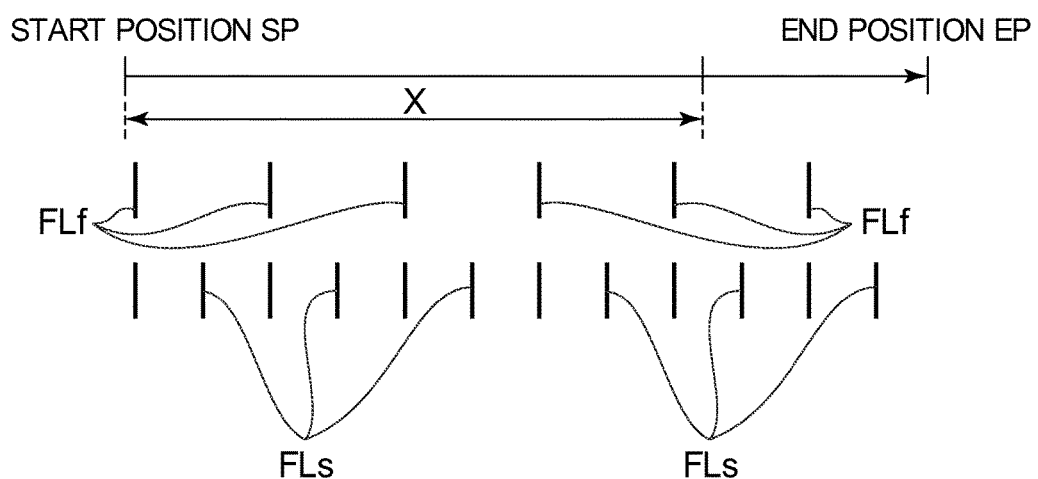
FIG. 7 is a view for explaining that the higher the moving velocity of the ultrasonic probe, the smaller the number of the frames included in the required range is and vice versa.

The number of frames Nf calculated by the projection data generation section 44 is smaller the higher the moving velocity of the ultrasonic probe 2, and becomes larger the lower the moving velocity of the ultrasonic probe 2. The explanation that follows is based on FIG. 7. Referring to FIG. 7, it is assumed that the ultrasonic probe 2 is moved from an ultrasonic scan start position SP to an ultrasonic scan end position EP. It is also assumed that within the range spanning the scan start position SP and scan end position EP, the range X is the above-mentioned required range. In FIG. 7, the crosswise direction represents distances. Reference character FLf conceptually denotes the position at which the echo signal of one frame is obtained when the ultrasonic probe 2 is moved at a velocity Vfast. Also, reference character FLs conceptually stands for the position at which the echo signal of one frame is acquired when the ultrasonic probe 2 is moved at a velocity Vslow that is lower than the velocity Vfast.

The number of the frames included in the range X is different between the case where the ultrasonic probe 2 is moved at the velocity Vfast and the case where the ultrasonic probe 2 is moved at the velocity Vslow. The higher the moving velocity of the ultrasonic probe 2, the smaller the number of frames included in the range X becomes; the lower the moving velocity of the ultrasonic probe 2, the larger the number of frames included in the range X. Accordingly, as calculated by the projection data generation section 44, the number Nf of the frames that fall into the required range is smaller the higher the moving velocity of the ultrasonic probe 2 and becomes larger the lower the moving velocity of the ultrasonic probe 2.

Specifically, the projection data generation section 44 calculates the number of frames Nf using the following Expression 1:

$$Nf = \alpha \times C \qquad \text{Expression 1}$$

In Expression 1, C stands for the correlation coefficient calculated through the above-described correlation calculation, and $0 < C < 1$. Also, $\alpha$ denotes a proportionality constant set in such a manner that the number of frames corresponding to the required range is reached at a given moving velocity.

It should be noted that the range including the frames of which the number is Nf is calculated using Expression 1 (i.e., range in the moving direction of the ultrasonic probe 2) need not be identical to the above-mentioned required range. The range need only be approximately the same as the required range (e.g., within setting error).

The projection data generation section 44 may also calculate the number of frames Nf using the following Expression 1':

$$Nf = a \times e^{\alpha \times C} \qquad \text{Expression 1'}$$

In Expression 1', a and a each denote a coefficient set in such manner that the number of frames corresponding to the required range is reached at a given moving velocity, and e represents the base of natural logarithm.

Next in step S3, the projection data generation section 44 generates projection data by selecting the contrast data of the frames of which the number is Nf was calculated earlier in step S2. That is, the projection data generation section 44 generates projection data by selecting the frames ranging from the first frame to the Nf-th frame. The first frame is on the side of the scan start position.

Figure 8:
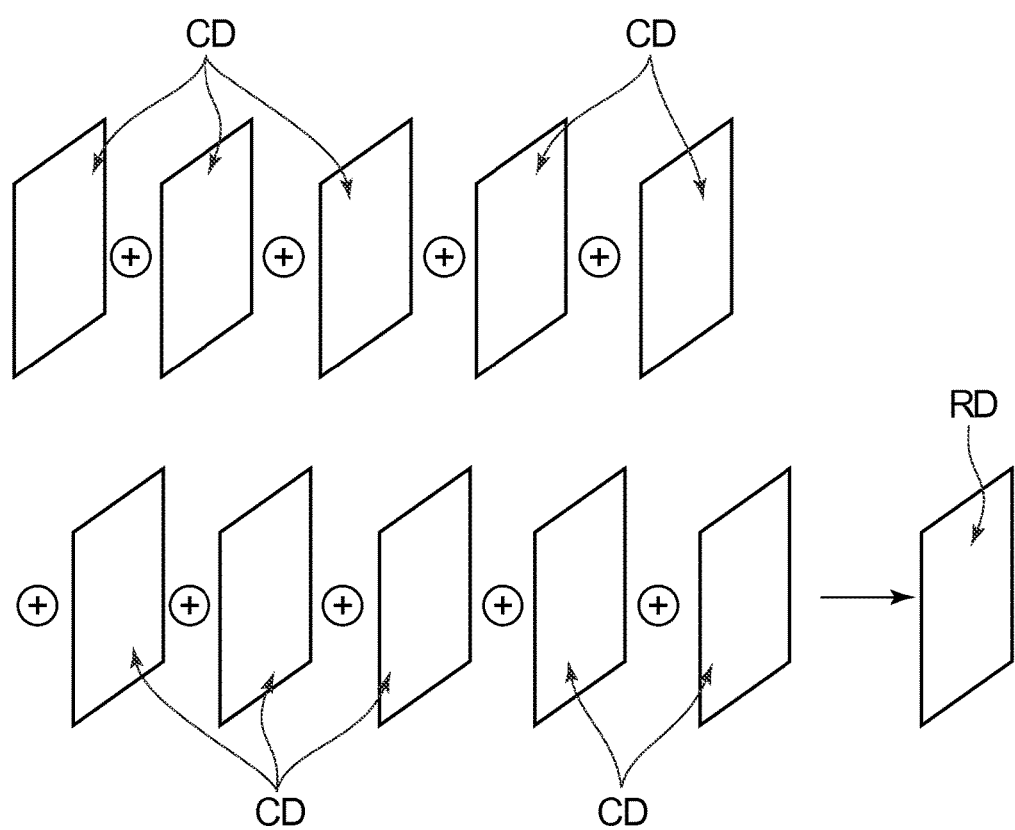
FIG. 8 is a view for explaining how projection data is generated by integrally adding up contrast data.

The projection data generation section 44 generates the projection data RD by integrally adding up the contrast data CD of the frames of which the number is Nf, as shown in FIG. 8 for example. In FIG. 8, the number of frames Nf is 10. The projection data generation section 44 integrally adds up the contrast data of the corresponding positions (pixels) across the frames involved.

Figure 9:
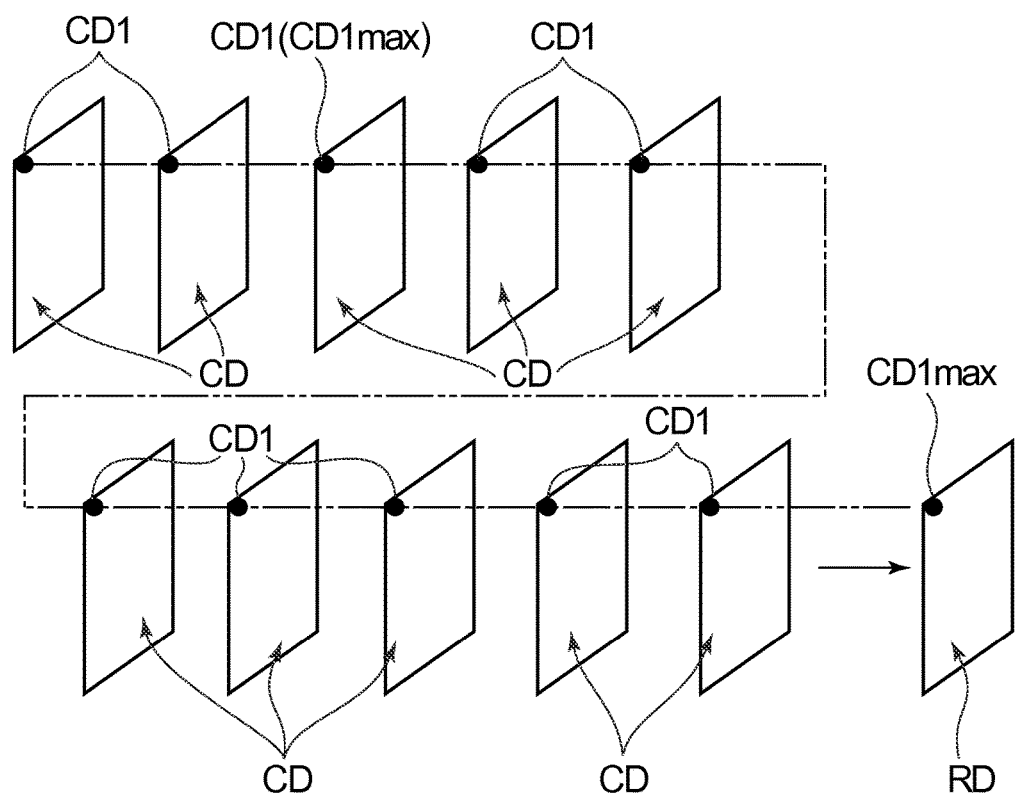
FIG. 9 is a view for explaining how projection data is generated by selecting the contrast data of maximum values from the contrast data of a plurality of frames.

The technique of generating the projection data RD is not limited to integral addition. For example, the projection data generation section 44 may generate the projection data RD by selecting maximum value contrast data CDmax from the contrast data CD of the frames of which the number is Nf. In this case, the projection data RD is made up of the maximum value contrast data CDmax within the range of the number of frames Nf. The projection data generation section 44 generates the projection data RD by selecting the maximum value contrast data CDmax at each corresponding position (pixel) on each frame. Where data at a given position is explained as shown in FIG. 9 for example, the data of the third frame is maximum value contrast data CD1max from among the contrast data CD1 at the corresponding positions across the frames involved. The contrast data CD1max constitutes the above-mentioned projection data RD.

Figure 10:
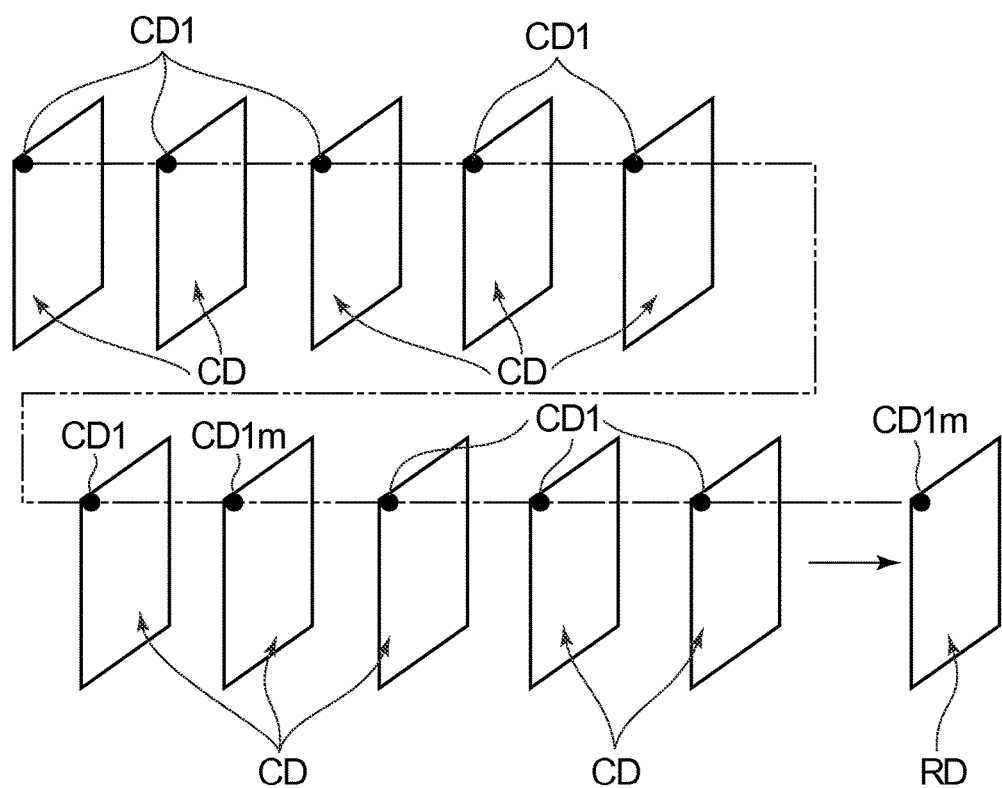
FIG. 10 is a view for explaining how projection data is generated by electing the contrast data of median values from the contrast data of a plurality of frames.

As another example, the projection data generation section 44 may also generate the projection data RD by selecting median value contrast data CDm from among the contrast data CD of the frames of which the number is Nf. In this case, the projection data RD is made up of the median value contrast data CDm within the range of the number of frames Nf. The projection data generation section 44 generates the projection data RD by selecting the median value contrast data CDm at each corresponding position (pixel) on each frame. Where data at a given position is explained as shown in FIG. 10 for example, the data of the seventh frame is median value contrast data CD1$m$ from among the contrast data CD1 at the corresponding positions across the frames involved. The contrast data CD1$m$ constitutes the above-mentioned projection data RD.

According to the ultrasonic diagnostic equipment 1 of this exemplary embodiment, the range in which to acquire the echo signals used for generating projection data is kept substantially constant regardless of the moving velocity of the ultrasonic probe 2 being varied.

Figure 11:
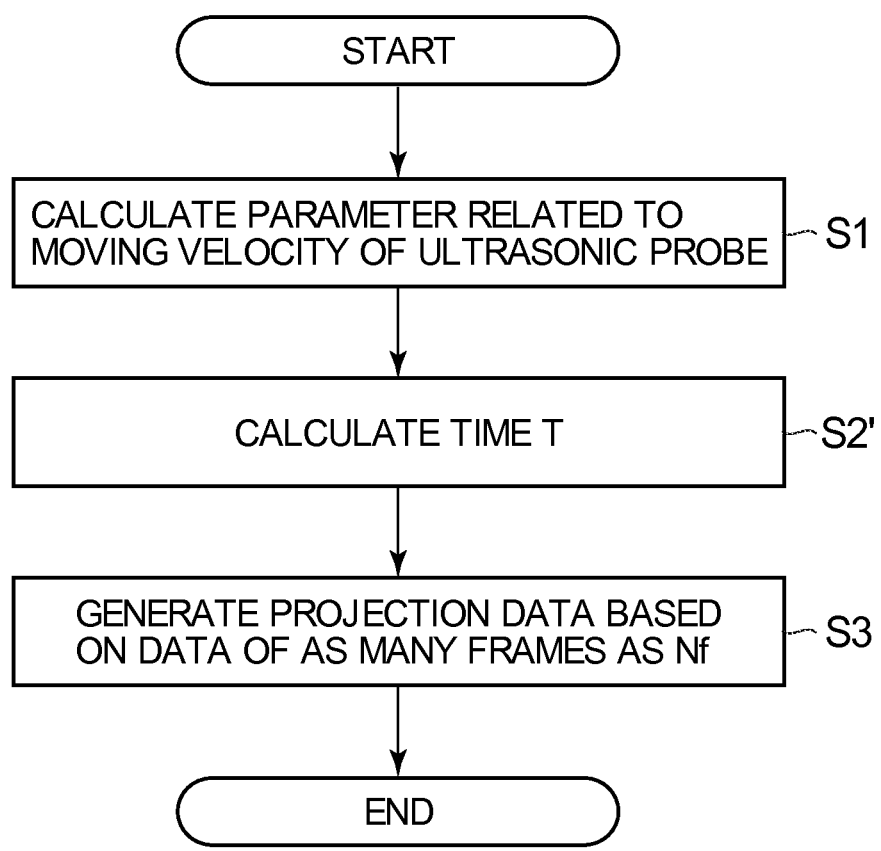
FIG. 11 is a flowchart showing a process for generating projection data in a first variation of the exemplary embodiment.

Some variations of the above-described exemplary embodiment are explained hereunder. A first variation is explained first. As shown in the flowchart of FIG. 11, the projection data generation section 44 may perform the process of step S2' in place of the process of step S2 discussed above. In step S2', the projection data generation section 44 calculates a time T instead of the number of frames Nf. That is, the projection data generation section 44 calculates the time T that includes the frames used for generating projection data based on the above-mentioned correlation coefficient C so that the range in which to acquire the echo signals of the frames for projection data generation becomes the required range discussed above.

The time T calculated by the projection data generation section 44 is shorter the higher the moving velocity of the ultrasonic probe 2, and becomes longer the lower the moving velocity of the ultrasonic probe 2. Specifically, the projection data generation section 44 calculates the time T using the following Expression 2:

$$T=\beta \times C \qquad \text{Expression 2}$$

In Expression 2, C denotes the above-mentioned correlation coefficient and $\beta$ represents a proportionality constant set in such a manner that the time corresponding to the required range is reached at a given moving velocity.

It should be noted that the range corresponding to the time T calculated using the Expression 2 in the moving direction of the ultrasonic probe 2 need not be identical to the above-mentioned required range. The range need only be approximately the same as the required range (e.g., within setting error).

The projection data generation section 44 may also calculate the time T using the following Expression 2':

$$T=b \times e^{\beta \times C} \qquad \text{Expression 2'}$$

In Expression 2', b and $\beta$ each denote a coefficient set in such manner that the time corresponding to the required range is reached at a given moving velocity.

Figure 12:
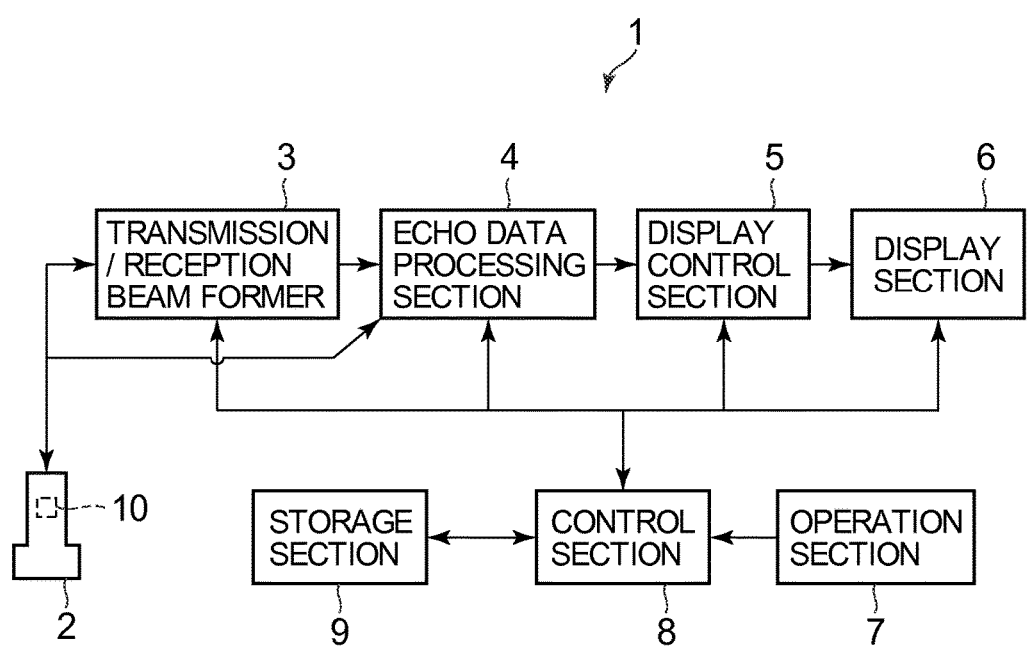
FIG. 12 is a diagram showing a typical overall structure of ultrasonic diagnostic equipment in a second variation of the exemplary embodiment.

A second variation is explained next. The parameter related to the moving velocity of the ultrasonic probe 2 and calculated in step S1 discussed above is not limited to the correlation coefficient. Alternatively, the parameter calculation section 43 may calculate the moving velocity itself of the ultrasonic probe 2 as the related parameter. In this case, as shown in FIG. 12, the ultrasonic probe 2 is equipped with an acceleration sensor 10 for detecting the moving velocity of the probe 2. The acceleration sensor 10 may also be incorporated in the ultrasonic probe 2. The acceleration sensor 10 is an example of the senor.

The parameter calculation section 43 in the echo data processing section 4 calculates the moving velocity of the ultrasonic probe 2 based on detection signals from the acceleration sensor 10.

After the moving velocity of the ultrasonic probe 2 has been calculated in step S1 above, the moving velocity V of the ultrasonic probe 2 is used in place of the correlation coefficient in step S2 or S2'. In this case, the projection data generation section 44 calculates the number of frames Nf using the following Expression 3 instead of Expression 1:

$$Nf=\alpha \times (1/V) \qquad \text{Expression 3}$$

In Expression 3, as Expression 1, $\alpha$ denotes a proportionality constant set in such a manner that the number of frames corresponding to the required range is reached at a given moving velocity.

Alternatively, the projection data generation section 44 may calculate the number of frames Nf using the following Expression 3' instead of Expression 1':

$$Nf=a \times e^{-\alpha \times V} \qquad \text{Expression 3'}$$

In Expression 3', as in Expression 1', a and $\alpha$ each denote a coefficient set in such manner that the number of frames corresponding to the required range is reached at a given moving velocity.

Also, the projection data generation section 44 may calculate the time T using the following Expression 4 instead of Expression 2:

$$T=\beta \times (1/V) \qquad \text{Expression 4}$$

In Expression 4, as in Expression 2, $\beta$ represents a proportionality constant set in such a manner that the time corresponding to the required range is reached at a given moving velocity.

Also, the projection data generation section 44 may calculate the time T using Expression 4' instead of Expression 2':

$$T=b \times e^{-\beta \times V} \qquad \text{Expression 4'}$$

In Expression 4', as in Expression 2', b and $\beta$ each denote a coefficient set in such manner that the time corresponding to the required range is reached at a given moving velocity.

Figure 13:
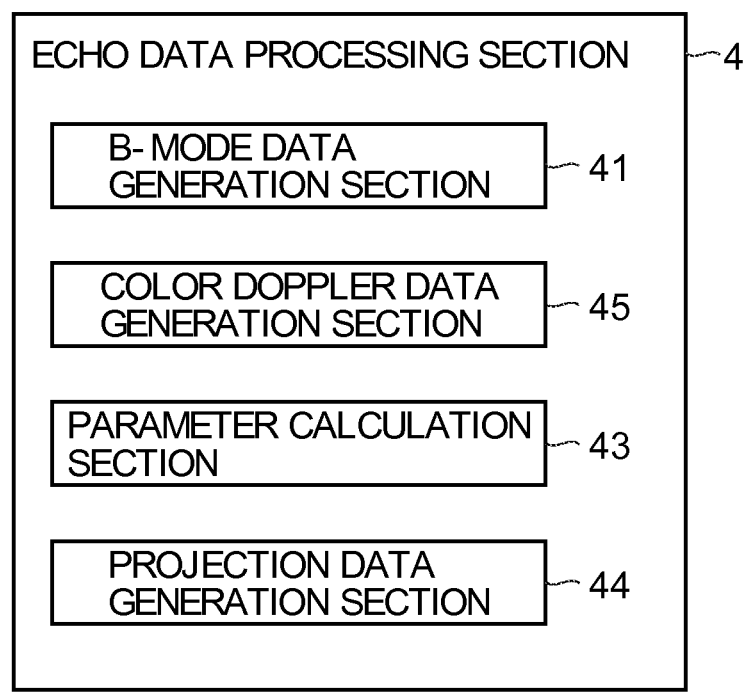
FIG. 13 is a block diagram showing another typical structure of the echo data processing section.

While an exemplary embodiment has been described using specific terms, such description is for illustrative purposes only. It is evident that changes and variations may be made without departing from the spirit and scope of the invention. For example, in generating the projection data, color Doppler data may be used in place of the contrast data. In this case, as shown in FIG. 13, the echo data processing section 4 includes a color Doppler data generation section 45 in place of the contrast data generation section 42.

The technique of generating the projection data RD is not limited to what has been discussed above. For example, the projection data RD may be generated by averaging the contrast data of the frames of which the number is Nf.

What is claimed is:

1. An ultrasonic image display apparatus for generating and displaying an ultrasonic image of a required range that covers a region interest of a test object, the apparatus comprising:
    an ultrasonic probe configured to:
        move in a translational displacement direction parallel to a surface of a test object, while in contact with the surface of the test object, from an ultrasonic scan start position (SP) to an ultrasonic scan end position (EP), and
        transmit and receive ultrasonic waves to and from the test object to obtain echo signals of a plurality of frames from a three-dimensional region of the test object;
    one or more processors a configured to:
        receive or set a required range in the translational displacement direction (X) that covers a region of interest within the three-dimensional region of the test object,
        receive, from the ultrasonic probe, echo signals of a plurality of frames from the three-dimensional region of the test object, obtained by the ultrasonic probe while moving the probe in the translational displacement direction from SP to EP, calculate a parameter related to a velocity of the ultrasonic probe moving in the translational displacement direction (V), where the parameter related to V is selected from a group consisting of a correlation coefficient between adjacent frames of the plurality of frames (C) and V, generate ultrasonic imaging data based on the echo signals of the plurality of frames so that the echo signals of the frames used for generating the ultrasonic imaging data are echo signals of frames acquired within X, by either:
(a): calculating a number of frames (Nf) of the plurality of frames included within X, wherein calculation of Nf is based on the calculated parameter related to V, where Nf is smaller the higher V is, and Nf is larger the lower V is, and
generating the ultrasonic imaging data based on echo signals of Nf frames included within X, or
(b): calculating an acquisition time duration (T) for when echo signals of frames included within X are obtained by the ultrasonic probe, wherein calculation of T is based on the calculated parameter related to V, where T is shorter the higher V is, and T is longer the lower V is, and
generating the ultrasonic imaging data based on echo signals of frames obtained during T, and generate an ultrasonic image based on the generated ultrasonic imaging data; and a display configured to display the generated ultrasonic image.

2. An ultrasonic image display apparatus according to claim 1, wherein the one or more processors is/are configured to generate the ultrasonic imaging data by adding up or averaging data derived from the echo signals that formed the basis of the ultrasonic imaging data generation.

3. An ultrasonic image display apparatus according to claim 1, wherein the one or more processors is/are configured to generate the ultrasonic imaging data based on data selected from data derived from the echo signals that formed the basis of the ultrasonic imaging data generation.

4. An ultrasonic image display apparatus according to claim 1, wherein the ultrasonic image generated based on the ultrasonic imaging data is a projection image obtained through projection of the three-dimensional region.

5. An ultrasonic image display apparatus according to claim 2, wherein the one of more processors is/are configured to calculate the parameter related to V by calculating C, wherein calculating C comprises performing a correlation calculation on data derived from the echo signals of the plurality of frames.

6. An ultrasonic image display apparatus according to claim 3, wherein the one of more processors is/are configured to calculate the parameter related to V by calculating C, wherein calculating C comprises performing a correlation calculation on the data derived from the echo signals of the plurality of frames.

7. An ultrasonic image display apparatus according to claim 4, wherein the one of more processors is/are configured to calculate the parameter related to V by calculating C, wherein calculating C comprises performing a correlation calculation on data derived from the echo signals of the plurality of frames.

8. An ultrasonic image display apparatus according to claim 2, wherein the one of more processors is/are is configured to calculate V as the parameter related to V, based on a detection signal from a sensor attached to the ultrasonic probe and configured to detect velocity of the sensor.

9. An ultrasonic image display apparatus according to claim 3, wherein the one of more processors is/are configured to calculate V as the parameter related to V, based on a detection signal from a sensor attached to the ultrasonic probe and configured to detect velocity of the sensor.

10. An ultrasonic image display apparatus according to claim 4, wherein the one of more processors is/are configured to calculate V as the parameter related to V, based on a detection signal from a sensor attached to the ultrasonic probe and configured to detect velocity of the sensor.

11. A method for operating an ultrasonic image display apparatus to generate and display an ultrasonic image of a required range that covers a region of interest of a test object, the method comprising:
transmitting and receiving ultrasonic waves to and from a test object using an ultrasonic probe to obtain echo signals of a plurality of frames from a three-dimensional region of the test object while moving the ultrasonic probe in a translational displacement direction parallel to a surface of the test object from an ultrasonic scan start position (SP) to an ultrasonic scan end position (EP) while the ultrasonic probe is in contact with the surface of the test object;
calculating, with one or more processors, a parameter related to a velocity of the ultrasonic probe moving in the translational displacement direction (V), where the parameter related to V is selected from a group consisting of a correlation coefficient between adjacent frames of the plurality of frames and V;
establishing a required range in the translational displacement direction (X) that covers a region of interest within the three-dimensional region of the test object;
generating, with one or more processors, ultrasonic imaging data based on the echo signals of the plurality of frames so that the echo signals of the frames used for generating the ultrasonic imaging data are echo signals of frames acquired within X, by either:
(a): calculating a number of frames (Nf) of the plurality of frames included within X, wherein calculation of Nf is based on the calculated parameter related to V, where Nf is smaller the higher V is, and Nf is larger the lower V is, and
generating the ultrasonic imaging data based on echo signals of Nf frames included within X, or
(b): calculating an acquisition time duration (T) for when echo signals of frames included within X, wherein calculation of T is based on the calculated parameter related to V, where T is shorter the higher V is, and T is longer the lower V is, and
generating the ultrasonic imaging data based on echo signals of frames obtained during T;
generating an ultrasonic image based on the generated ultrasonic imaging data; and
displaying the generated ultrasonic image.

12. An ultrasonic image display apparatus for generating and displaying an ultrasonic image of a required range that covers a region interest of a test object, the apparatus comprising:
an ultrasonic probe configured to:
be held by an operator,
be moved by the operator in a direction while in contact with a test object, from an ultrasonic scan start position (SP) to an ultrasonic scan end position (EP), and transmit and receive ultrasonic waves to and from the test object to obtain echo signals of a plurality of frames from a three-dimensional region of the test object;

one or more processors configured to:
receive or set a required range in the direction (X) that covers a region of interest within the three-dimensional region of the test object, receive, from the ultrasonic probe, echo signals of a plurality of frames from the three-dimensional region of the test object, obtained by the ultrasonic probe while the operator moves the ultrasonic probe in the direction from SP to EP, calculate a parameter related to a velocity of the ultrasonic probe moving in the direction (V), where the parameter related to V is selected from a group consisting of a correlation coefficient between adjacent frames of the plurality of frames (C) and V;

generate ultrasonic imaging data based on the echo signals of the plurality of frames so that the echo signals of the frames used for generating the ultrasonic imaging data are echo signals of frames acquired within X, by either:

(a): calculating a number of frames (NO of the plurality of frames included within X, wherein calculation of Nf is based on the calculated parameter related V, where Nf is smaller the higher V is, and Nf is larger the lower V is, and generating the ultrasonic imaging data based on echo signals of Nf frames including within X, or (b): calculating an acquisition time duration (T) for when echo signals of frames included within X are obtained by the ultrasonic probe, wherein the calculation of T is based on the calculated parameter related to V, where T is shorter the high V is, and T is longer the lower V is, and generating the ultrasonic imaging data based on echo signals of frames obtained during T, and generate an ultrasonic image based on the generated ultrasonic imaging data; and a display configured to display the generated ultrasonic image.

* * * * *